(12) United States Patent
Hsi et al.

(10) Patent No.: US 11,564,820 B2
(45) Date of Patent: Jan. 31, 2023

(54) URETERAL STENT AND RELATED METHODS

(71) Applicant: Regents of the University of California, Oakland, CA (US)

(72) Inventors: Ryan Hsi, Nashville, TN (US); Marshall Stoller, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 600 days.

(21) Appl. No.: 16/328,349

(22) PCT Filed: Sep. 1, 2017

(86) PCT No.: PCT/US2017/049883
§ 371 (c)(1),
(2) Date: Feb. 26, 2019

(87) PCT Pub. No.: WO2018/045301
PCT Pub. Date: Mar. 8, 2018

(65) Prior Publication Data
US 2021/0259863 A1  Aug. 26, 2021

Related U.S. Application Data

(60) Provisional application No. 62/382,833, filed on Sep. 2, 2016.

(51) Int. Cl.
| | | |
|---|---|---|
| *A61F 2/94* | (2013.01) | |
| *A61F 2/04* | (2013.01) | |
| *A61F 2/95* | (2013.01) | |
| *A61F 2/82* | (2013.01) | |

(52) U.S. Cl.
CPC .............. *A61F 2/94* (2013.01); *A61F 2/04* (2013.01); *A61F 2/95* (2013.01); *A61F 2002/048* (2013.01); *A61F 2002/826* (2013.01); *A61F 2210/009* (2013.01); *A61F 2220/0008* (2013.01); *A61F 2220/0075* (2013.01); *A61F 2250/0018* (2013.01); *A61F 2250/0098* (2013.01)

(58) Field of Classification Search
CPC .... A61F 2/82; A61F 2/04; A61F 2/852; A61F 2002/048; A61F 2002/826; A61F 2002/828; A61F 2210/009; A61F 2/94; A61F 2/95; A61F 2220/0008; A61F 2220/0075; A61F 2250/0018; A61F 2250/0098
See application file for complete search history.

(56) References Cited

U.S. PATENT DOCUMENTS

| | | | |
|---|---|---|---|
| 4,790,809 A | 12/1988 | Kuntz | |
| 4,790,810 A | 12/1988 | Pugh, Jr. et al. | |
| 6,395,021 B1 | 5/2002 | Hart et al. | |
| 10,307,564 B2 * | 6/2019 | Erbey, II | A61M 25/0026 |
| 10,994,109 B2 * | 5/2021 | Hakim | A61F 2/04 |
| 11,439,493 B2 * | 9/2022 | Smouse | A61F 2/04 |
| 2002/0138154 A1 | 9/2002 | Li et al. | |

(Continued)

*Primary Examiner* — Suzette J Gherbi
(74) *Attorney, Agent, or Firm* — Sean D. Solberg

(57) ABSTRACT

The embodiments disclosed herein relate to a ureteral stent having two stent bodies and a tether. The stent can minimize or prevent migration of the device out of the bladder of the patient while also reducing patient discomfort associated with such stents.

18 Claims, 3 Drawing Sheets

(56) References Cited

U.S. PATENT DOCUMENTS

| | | | |
|---|---|---|---|
| 2005/0240278 A1* | 10/2005 | Aliski | A61F 2/04 |
| | | | 604/8 |
| 2012/0157833 A1 | 6/2012 | Berent et al. | |
| 2014/0135941 A1 | 5/2014 | Smouse et al. | |
| 2017/0095651 A1* | 4/2017 | Hutchins, III | A61M 31/002 |
| 2021/0007870 A1* | 1/2021 | Smouse | A61M 27/008 |
| 2022/0125570 A1* | 4/2022 | Stifelman | A61F 2/04 |

* cited by examiner

URETERAL STENT AND RELATED METHODS

CROSS-REFERENCE TO RELATED APPLICATION(S)

This application claims priority to International PCT Application No. PCT/US17/49883, filed on Sep. 1, 2017, which claims benefit to U.S. Provisional Application 62/382,833, filed Sep. 2, 2016 and entitled "Ureteral Stent and Related Methods," which is hereby incorporated herein by reference in its entirety.

FIELD OF THE INVENTION

The various embodiments herein relate to an improved stent, including, for example, a ureteral stent.

BACKGROUND OF THE INVENTION

For a patient with an obstructed ureter, a ureteral stent is used to aid in transfer of urine from one of the patient's kidneys to the patients bladder through the obstructed ureter. As best shown in FIG. 1B, the ureters 20, 22 connect the kidneys 24, 26, respectively, to the bladder 28 for the drainage of urine from the kidneys 24, 26 to the bladder 28. Ureter obstruction can occur as a result of one or more kidney stones, stricture, tumors, or scarring from various causes, including infection, surgery, or radiation. While aiding with the flow of urine to the bladder, the stent should also function to stay in the desired position within the ureter and not migrate out of or further into the kidney or the bladder. "Stent migration" is a phenomenon in which the end of the stent positioned in the bladder or kidney moves or "migrates" into and/or through the ureter, thereby resulting in the failure of the stent to provide the desired urinary diversion from the kidney to the bladder.

As shown in FIG. 1A, one typical design of a known ureteral stent 10 that is configured to aid flow while maintaining its position has a hollow tubular stent body 12 with having spirals or loops 14, 16 at both ends. The stent body 12 can also be solid (have no lumen therein). The first self-contained loop (also referred to as a "first loop," "first coil," "renal loop," or "renal coil") 14 is coupled to or integral with one end of the body 12, and the second self-contained loop (also referred to as a "second loop," "second coil," "bladder loop," or "bladder coil") 16 is coupled to or integral with the other end. Other structures/configurations other than loops are also used in various known stents.

In use, as shown in FIG. 1B, when the stent 10 is successfully implanted into the patient, the renal loop 14 is positioned in the kidney 26 or renal pelvis, the body 12 is positioned in and through the ureter 22, and the bladder loop 16 is positioned in the bladder 28. The loops 14, 16 (or other types of configurations/structures) function to retain the stent 10 in its desired position, with the first loop 14 being retained in the kidney 26 and the second loop 16 being retained in the bladder 28. The loops 14, 16 are formed as a result of both ends of the stent 10 deviating from a substantially linear or tubular shape and instead forming structures that reduce the risk of migration of the stent 10. It is understood that while the stent 10 is positioned in the left ureter 22 as shown, it can also be positioned in the right ureter 20 in the same fashion as described herein. A stent can be required for a period ranging from a day to several months.

In this type of stent 10, the urine flows through the lumen (not shown) of the tubular stent body 12 such that the wall of the body 12 prevents obstructions from blocking the flow. Alternatively, the urine can flow around or external to the tubular stent body 12. Thus, the body 12 in these various types of stents 10 can have a small or large lumen diameter (typically ranging from about 3.7 French up to about 10 French).

One disadvantage of this type of stent is patient discomfort. Typically, the above stent type causes pain or discomfort due to the bladder loop irritating, scratching, puncturing, or poking the bladder lining. While the loop prevents or reduces the incidence of stent migration, the loop can cause debilitating pain.

Another typical design of a ureteral stent has a highly flexible strands or loops at the bladder end of the stent (replacing the standard loop described above) that reduce the size of the stent in the bladder end to reduce patient discomfort. More specifically, this type of stent has a renal end that is substantially similar to the renal end of the stent type described above, but at some (usually significant) distance from the renal end, the flexible strands or loops are coupled thereto or integrated therein—typically at about the iliac vessels of the patient when the stent is properly positioned in the patient.

One disadvantage of this type of stent is that stents of multiple sizes are required and then a physician must select the stent size to use based on approximations of the patient's physiology. Further, despite the reduced size of the strands or loops, significant patient discomfort is still a common problem, and there is little evidence that these alternative stent designs reduce stent discomfort. In these designs, the common feature is the presence of a bulky bladder component that causes bladder pain.

While multiple designs have been tested, no stent configuration to date has been able to successfully overcome both the migration problem and the patient discomfort associated with the various structures/configurations (such as the loop or highly flexible strands/loops described above) used to prevent the migration.

There is a need in the art for an improved ureteral stent and related systems and methods.

BRIEF SUMMARY OF THE INVENTION

Discussed herein are various devices and methods for promoting flow of urine through the ureter to the bladder of a patient.

In Example 1, a ureteral stent comprises a first tubular stent body comprising a first lumen, a first retention structure extending from a distal end of the first tubular stent body, a second tubular stent body comprising a second lumen, a second retention structure extending from a distal end of the second tubular stent body, and a connection member comprising a first end extending from a proximal end of the first tubular stent body, and a second end extending from a proximal end of the second tubular stent body.

Example 2 relates to the ureteral stent according to Example 1, wherein the first tubular stent body, the second tubular stent body, and the connection member form a unitary component.

Example 3 relates to the ureteral stent according to Example 1, wherein the first end of the connection member is coupled to the proximal end of the first tubular stent body and the second end of the connection member is coupled to the proximal end of the second tubular stent body.

Example 4 relates to the ureteral stent according to Example 3, wherein the connection member comprises a cord, a string, a monofilament, or a braided material.

Example 5 relates to the ureteral stent according to Example 1, wherein the connection member comprises a first portion comprising the first end extending from the proximal end of the first tubular stent body, and a second portion comprising the second end extending from the proximal end of the second tubular stent body, wherein the first and second portions are magnetically coupleable.

Example 6 relates to the ureteral stent according to Example 1, wherein the connection member is configured to prevent distal migration of the first and second tubular stent bodies.

Example 7 relates to the ureteral stent according to Example 1, further comprising openings defined in the first tubular stent body and he second tubular stent body.

Example 8 relates to the ureteral stent according to Example 7, wherein the openings provide fluidical access to the first and second lumens.

In Example 9, a ureteral stent comprises a first tubular stent body comprising a first lumen, a first retention structure extending from a distal end of the first tubular stent body, a connection member comprising a first end extending from a proximal end of the first tubular stent body, a second tubular stent body comprising a second lumen, and a second retention structure extending from a distal end of the second tubular stent body. A second end of the connection member extends from a proximal end of the second tubular stent body. Further, the first tubular stent body is disposable within a first ureter, the first retention structure is disposable within a first kidney, at least a portion of the connection member is disposable within a bladder, the second tubular stent body is disposable within a second ureter, and the second retention structure is disposable within a second kidney.

Example 10 relates to the ureteral stent according to Example 9, wherein the connection member is a unitary component.

Example 11 relates to the ureteral stent according to Example 10, wherein the connection member comprises a lumen.

Example 12 relates to the ureteral stent according to Example 9, wherein the first end of the connection member is coupled to the proximal end of the first tubular stent body and the second end of the connection member is coupled to the proximal end of the second tubular stent body.

Example 13 relates to the ureteral stent according to Example 12, wherein the connection member comprises a cord, a string, a monofilament, or a braided material.

Example 14 relates to the ureteral stent according to Example 9, wherein the connection member comprises a first portion comprising the first end coupled to the proximal end of the first tubular stent body and a second portion comprising the second end coupled to the proximal end of the second tubular stent body, wherein the first and second portions are magnetically coupleable.

Example 15 relates to the ureteral stent according to Example 9, wherein the connection member comprises a first portion and a second portion. The first portion comprises the first end coupled to the proximal end of the first tubular stent body, and a first magnet coupled to the first portion. The second portion comprises the second end coupled to the proximal end of the second tubular stent body, and a second magnet coupled to the second portion, wherein the second magnet is magnetically coupled with the first magnet.

Example 16 relates to the ureteral stent according to Example 9, wherein the connection member is configured to prevent distal migration of the first and second tubular stent bodies.

In Example 17, a method of promoting flow of urine to a bladder comprises inserting a first guidewire into a first kidney via a first ureter, inserting a second guidewire into a second kidney via a second ureter, and urging a first tubular stent body distally on the first guidewire until a first retention structure extending from a distal end of the first tubular stent body is disposed in the first kidney. The first tubular stent body comprises a first lumen. The method further comprises urging a second tubular stent body distally on the second guidewire until a second retention structure extending from a distal end of the second tubular stent body is disposed in the second kidney. The second tubular stent body comprises a second lumen. At least a portion of a connection member is disposable within the bladder when the first retention structure is disposed in the first kidney and the second retention structure is disposed in the second kidney, and the connection member comprises a first end coupled to a proximal end of the first tubular stent body and a second end coupled to a proximal end of the second tubular stent body.

Example 18 relates to the method according to Example 17, further comprising magnetically coupling a first portion of the connection member to a second portion of the connection member in the bladder.

Example 19 relates to the method according to Example 17, further comprising urging the connection member proximally out of the bladder to remove the connection member, the first tubular stent body, and the second tubular stent body from the patient.

Example 20 relates to the method according to Example 17, wherein the connection member prevents distal migration of the first and second tubular stent bodies.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments disclosed herein relate to a ureteral stent that minimizes or prevents migration of the stent body out of the bladder (and into the ureter) while also reducing or eliminating the discomfort resulting from known ureteral stents.

Figure 1A:
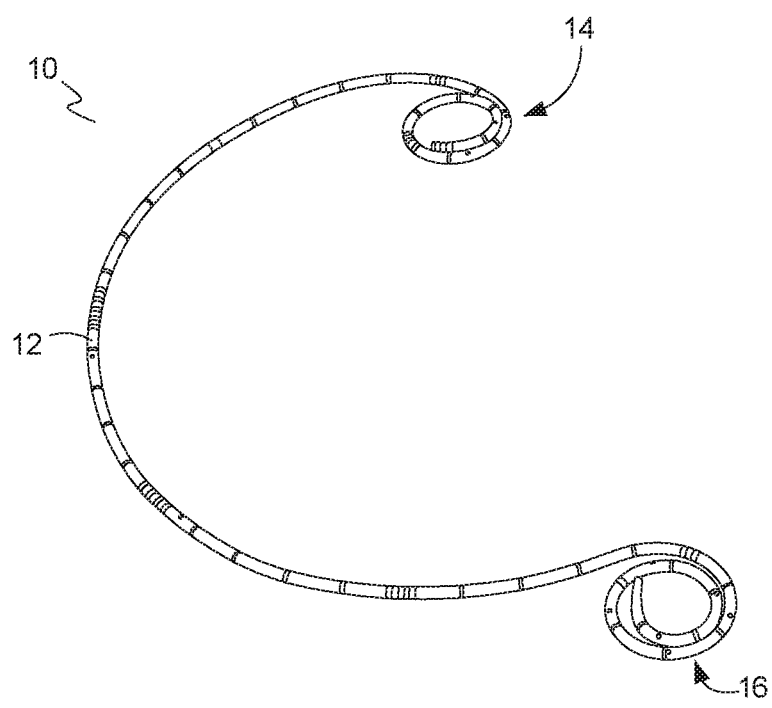
FIG. 1A is a perspective view of a known ureteral stent.
Figure 1B:
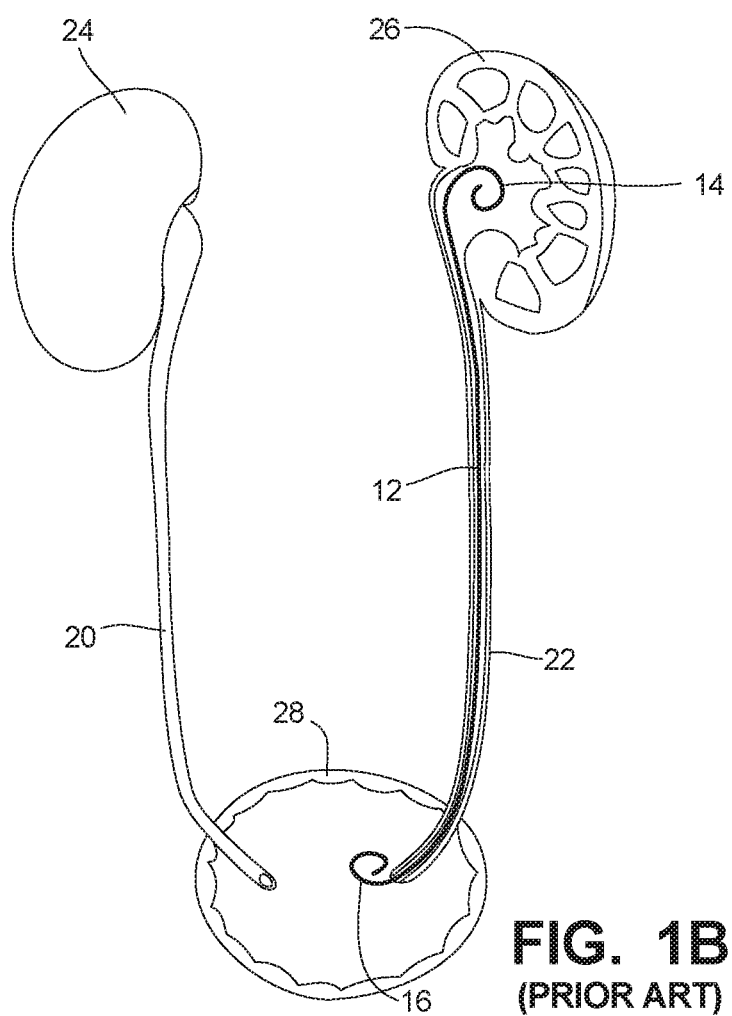
FIG. 1B is a cross-sectional schematic view of the known ureteral stent of FIG. 1A implanted in the ureter of a patient.
Figure 2:
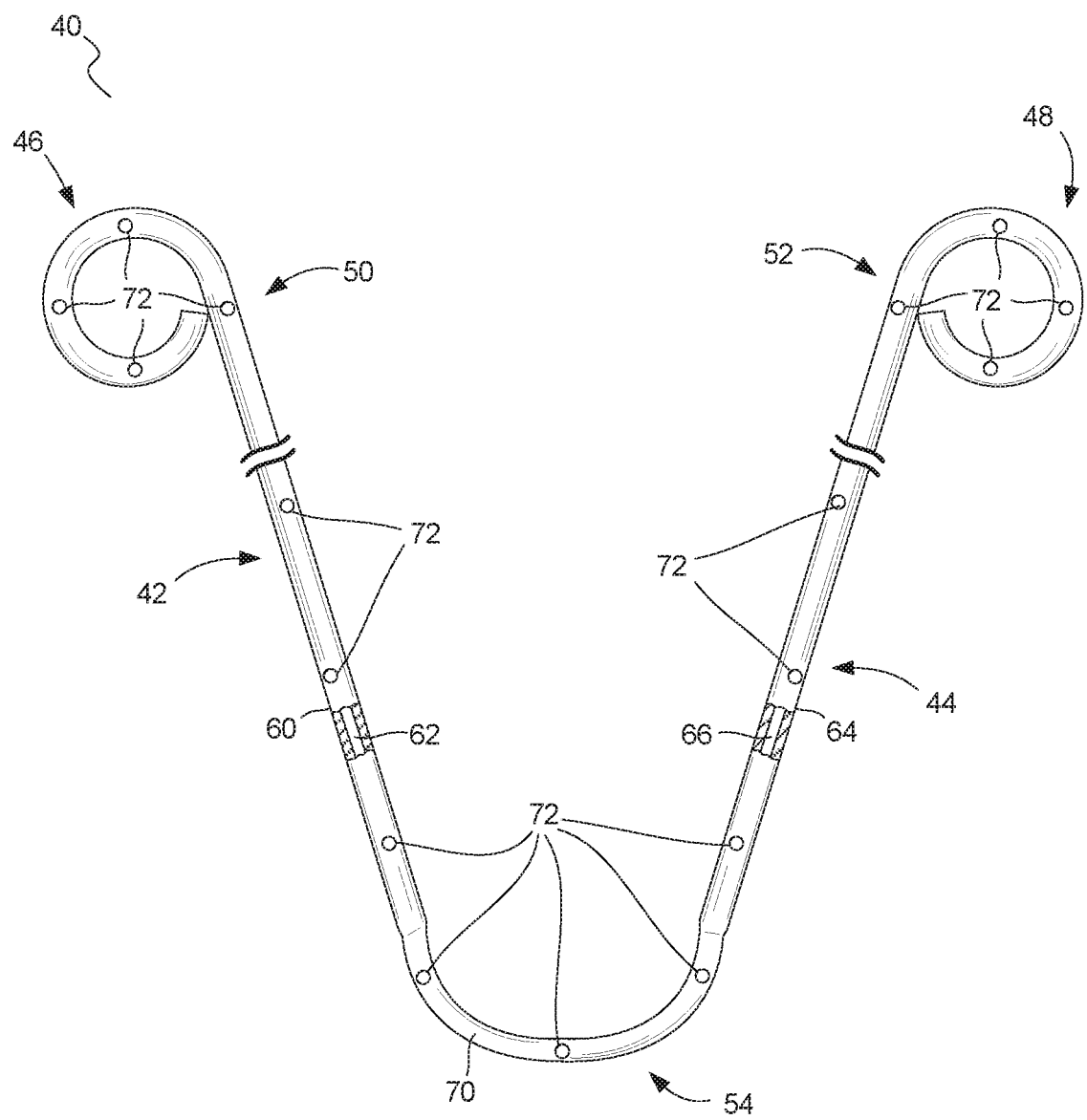
FIG. 2 is a front view of a ureteral stent, according to one embodiment.

FIG. 2 depicts a ureteral stent 40, according to one embodiment. The stent 40 has a first tubular stent body (or "right stent body") 42 and a second tubular stent body (or "left stent body") 44. The right stent body 42 has a first retention structure (or "right retention structure") 46 extending from or at the distal end 50 of the body 42, while the left stent body 44 has a second retention structure (or "left retention structure") 48 extending from or at the distal end 52 of the body 44. In addition, the stent 40 has a connection member (also referred to herein as a "tether" or "third retention structure") 54 coupled to, extending from, or integral with the proximal ends of the right and left stent bodies 42, 44.

In the instant Application, the ends of the stent bodies (such as stent bodies 42, 44) that are positioned in the kidneys will be referred to as the "distal" ends of those bodies because those ends are the ends that are typically first inserted into the patient. However, it is understood that others may refer to the ends positioned in the kidneys as "proximal" ends. The terms used herein are not intended to be limiting, but instead are intended to identify the various components of the various embodiments herein in a fashion that allows for the various components to be easily identified in relation to each other.

In accordance with on implementation, the right stent body 42 is a tubular body 42 having a tubular wall 60 that defines a lumen 62. Similarly, the left stent body 44 is a tubular body 44 having a tubular wall 64 that defines a lumen 66. In one implementation, the outer diameter of the tubular bodies 42, 44 can range from 3 to 10 French. Further, certain embodiments of the bodies 42, 44 have a length ranging from about 10 to 32 cm. According to certain embodiments, the bodies 42, 44 can be made of one or more thermoplastic materials (such as, for example, polyurethranes), one or more thermoset elastomers (such as, for example, silicone), one or more hydrogels, one or more metal alloys, one or more biodegradable materials, or one or more other polymers (such as, for example, polyisobutylene, polyacticacid, polyglycolic acid, poly styrene, and/or polymethylmethacrylate). In one implementation, regardless of the material selected, it is radiopaque so that the material can be visualized within the patient's body using imaging technology. Alternatively, it is understood that the right and left stent bodies 42, 44 can have the structure and/or features of any ureteral tube with a lumen in any known ureteral stent.

In the specific exemplary embodiment discussed above and depicted in FIG. 2, the right and left retention structures 46, 48 are renal coils 46, 48 having known renal coil structures. According to one implementation, each of the coils 46, 48 can have a curl diameter ranging from about 2 to 5 cm. According to certain embodiments, the coils 46, 48 can be made of the same or similar materials as those described above with respect to the bodies (such as bodies 42, 44). In one implementation, regardless of the material selected, it is radiopaque so that the material can be visualized within the patient's body using imaging technology. Alternatively, it is understood that the right and left retention structures 46, 48 can be any known retention structure having any known structure and/or features that is positioned in a kidney to aid in retention of a ureteral stent in its desired implanted position.

The stent 40, according to one implementation, has multiple openings 72 defined in the stent 40 as shown in FIG. 2. For example, the right and left stent bodies 42, 44 have openings 72 defined in the tubular walls 60, 64 such that the openings 72 are in fluidic communication with the lumens 62, 66 therein. According to one embodiment, the openings 72 allow fluid to pass into and out of the lumens 62, 66 of the right and left stent bodies 42, 44.

According to certain implementations, the tether 54 as shown is a tubular component 54 having a lumen 70 defined therein. In one embodiment, the tether 54 has a similar or smaller diameter in comparison to the right and left stent bodies 42, 44. That is, the tether 54 has a diameter ranging from about 3 French to about 10 French. In further implementations, the tether 54 is softer and/or more flexible or pliable than the right and left stent bodies 42, 44. Alternatively, the tether 54 has no lumen. In a further alternative, the tether 54 is a cord or string. The tether 54 can be made of the same or similar materials as those described above with respect to the bodies (such as bodies 42, 44) and the coils (such as coils 46, 48). Further, the tether 54 can also be made of a monofilament or braided material such as silk or nylon. In one implementation, regardless of the material selected, it can be radiopaque so that the material can be visualized within the patient's body using imaging technology. Alternatively, the tether 54 is not radiopaque.

In accordance with some implementations, the tether 54 is a separate component that is coupled at a first end to the proximal end of the right stent body 42 and at a second end to the proximal end of the left stent body 44. Alternatively, the tether 54 is integral with the right and left stent bodies 42, 44 such that the right stent body 42, the tether 54, and the left stent body 44 are a single unitary component.

Figure 3:
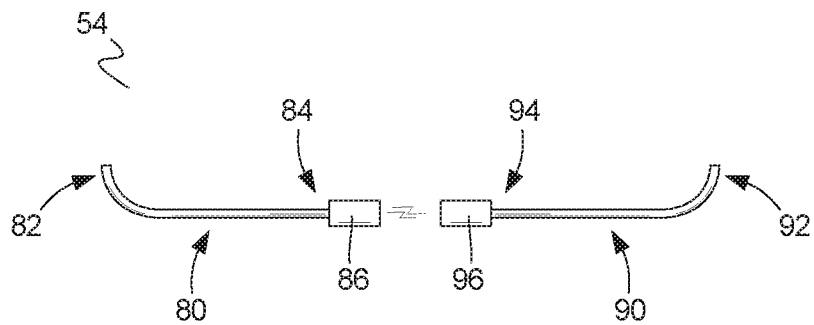
FIG. 3 is a front view of a tether of a ureteral stent, according to one embodiment.

According to other embodiments as best shown in FIG. 3, the tether 54 is made up of two components: a first portion 80 having a first magnetic component 86 at a second end 84 of the portion 80 and a second portion 90 having a second magnetic component 96 at a second end 94 of the portion 90. The first and second magnetic components 86, 96 are configured to be coupleable with each other. The first portion 80 is coupled at the first end 82 to the proximal end of the right stent body 42, while the second portion 90 is coupled at the first end 92 to the proximal end of the left stent body 44. Alternatively, the first portion 80 is integral with the right stent body 42 such that the right stent body 42 and the first portion 80 are a single unitary component, and the second portion 90 is integral with the left stent body 44 such that the left stent body 44 and the second portion 90 are a single unitary component.

Figure 4:
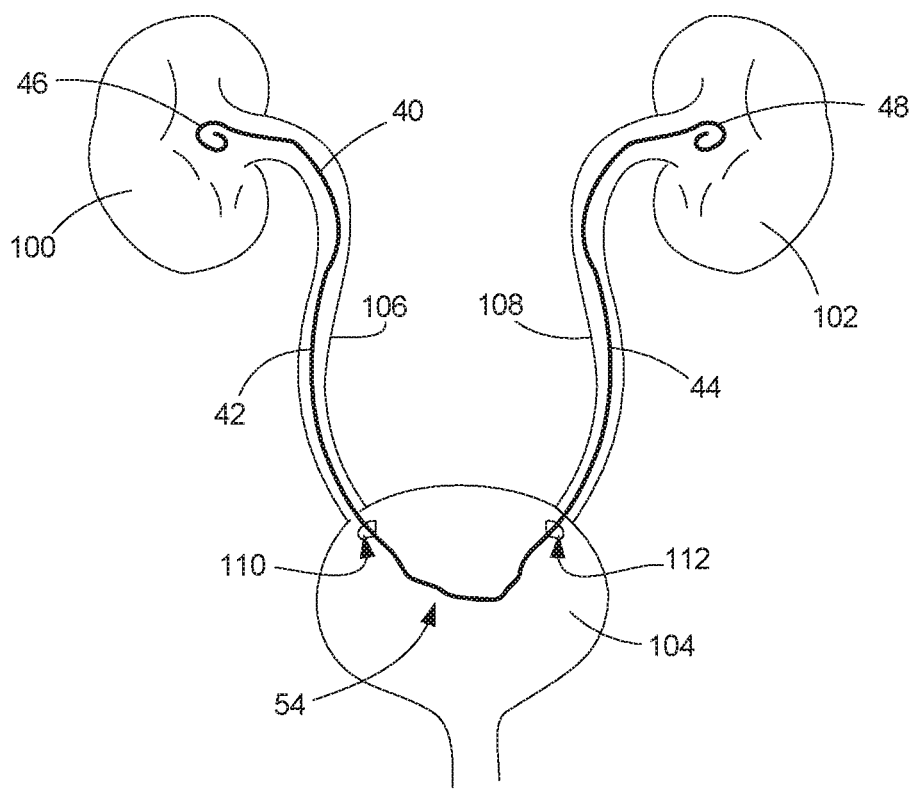
FIG. 4 is a cross-sectional schematic view of the ureteral stent of FIG. 2 implanted in a patient, according to one embodiment.

As best shown in FIG. 4, in use according to one embodiment, the stent 40 can be positioned in the patient as depicted to aid the flow of urine from one or both of the kidneys 100, 102 to the bladder 104. More specifically, the right and left retention structures 46, 48 are positioned in the right and left kidneys 100, 102, respectively, and the right and left stent bodies 42, 44 are positioned in the right and left ureters 106, 108, respectively. Further, the tether 54 is positioned in the bladder 104.

It is understood that the right and left retention structures 46, 48 are typically positioned entirely within the kidneys 100, 102 to help retain the stent 40 in its desired position. However, it is further understood that portions of the structures 46, 48 coupled to or integral with the stent bodies 42, 44 may extend out of the kidneys 100, 102 and into the ureters 106, 108. In addition, it is understood that, in other embodiments, portions of the stent bodies 42, 44 that are coupled to or integral with the retention structures 46, 48 may extend from the ureters 106, 108 into the kidneys 100, 102. Similarly, it is understood that portions of the stent bodies 42, 44 that are coupled to or integral with the tether 54 may extend into the bladder 104 through the ureteral orifices 110, 112, and that, in other implementations, portions of the tether 54 that are coupled to or integral with the stent bodies 42, 44 may extend into the right and left ureters 106, 108 through the ureteral orifices 110, 112.

The various stent embodiments disclosed or contemplated herein, including, for example, stent 40, reduce the patient discomfort prevalent in known ureteral stents while also preventing migration of the stent 40 out of the bladder. These two benefits are accomplished via the use of the two ureteral stent bodies 42, 44 that are coupled together by the tether 54 in the bladder 104, thereby eliminating the need for a standard bladder coil positioned in the bladder as described above in the Background. The elimination of the bladder coil reduces the incidence of injury to the bladder lining or the bladder that is typically caused by such a coil, thereby reducing the pain associated with such injury. In addition, the tether 54 prevents migration without the associated pain of known stents by coupling together the two stent bodies 42, 44, which are retained in their desired positions by the retention members 46, 48 in the kidneys 100, 102.

One method of implanting the stent 40, according to one embodiment, includes the following steps. First, two guidewires (not shown) are positioned into the right and left kidneys 100, 102 through the right and left ureters 106, 108 via the urethra and the bladder such that one guidewire is positioned in one kidney 100 and the other guidewire is positioned in the other kidney 102. Once the guidewires are positioned into the kidneys 100, 102, the distal ends of the stent bodies 42, 44—including the right and left retention structures 46, 48—are simultaneously loaded onto (or otherwise positioned over) the proximal ends of the two guidewires. As the stent bodies 42, 44 are advanced distally over the guidewires, the proximal ends of the guidewires (not shown) extend out of two sideholes (not shown) defined in the tether 54 that allow for the stent bodies 42, 44 and tether 54 to be advanced. Once the bodies 42, 44 and tether 54 have been advanced to the point that the guidewires (not shown) extend out of the sideholes (not shown), one or two known pusher devices (not shown) can be positioned on and advanced distally over the guidewires (not shown) behind the stent bodies 42, 44 and tether 54 such that the advancement of the pusher device (not shown) urges the stent bodies 42, 44 and tether 54 distally. The stent bodies 42, 44 are advanced distally until the right and left retention structures 46, 48 are positioned in the kidneys as desired. X-ray, ultrasound, or some other imaging technology can be used to determine that the right and left retention structures 46, 48 are positioned as desired. Once the right and left retention structures 46, 48—and thus the stent bodies 42, 44 and tether 54—are positioned correctly, the guidewires (not shown) can be removed, leaving the stent 40 in place.

In an alternative method in which the stent 40 has two stent bodies 42, 44 that can be removably coupled together at the tether 54 via magnets (such as magnets 86, 96 as discussed above), the two bodies 42, 44 can be advanced separately over the two guidewires (not shown) and positioned as desired. Once the retention structures 46, 48 and the stent bodies 42, 44 are positioned correctly, the magnets (such as magnets 86, 96, for example) on the proximal end of the bodies 42, 44 are coupled together in the bladder 104.

In accordance with one embodiment, the stent 40 can be removed using a small removal tether (not shown). That is, the stent 40 can have a removal tether (not shown) coupled to the tether 54 such that the removal tether (not shown) extends away from the stent 40 (and in some embodiments extends out of the urethra) and can be grasped or captured and then a proximal force can be applied to the removal tether to remove the stent 40 from the patient.

Alternatively, the stent 40 can be removed by using a tool of some kind. The tool can be inserted into the bladder and grasp the tether 54 of the stent and then be urged proximally to remove the stent 40.

Although the present invention has been described with reference to preferred embodiments, persons skilled in the art will recognize that changes may be made in form and detail without departing from the spirit and scope of the invention.

What is claimed is:

1. A ureteral stent, comprising:
   (a) a first tubular stent body comprising a first lumen;
   (b) a first retention structure extending from a distal end of the first tubular stent body;
   (c) a second tubular stent body comprising a second lumen;
   (d) a second retention structure extending from a distal end of the second tubular stent body; and
   (e) an elongate connection member comprising:
      (i) a first length extending from a proximal end of the first tubular stent body such that the first length and the first tubular stent body form a first single unitary component; and
      (ii) a second length extending from a proximal end of the second tubular stent body such that the second length and the second tubular stent body form a second single unitary component,
   wherein the first and second lengths are coupleable.

2. The ureteral stent of claim 1, wherein the connection member is configured to prevent distal migration of the first and second tubular stent bodies.

3. The ureteral stent of claim 1, further comprising openings defined in the first tubular stent body and the second tubular stent body.

4. The ureteral stent of claim 3, wherein the openings provide fluidic access to the first and second lumens.

5. A ureteral stent, comprising:
   (a) a first tubular stent body comprising a first lumen, wherein the first tubular stent body is disposable within a first ureter;
   (b) a first retention structure extending from a distal end of the first tubular stent body, wherein the first retention structure is disposable within a first kidney;
   (c) a second tubular stent body comprising a second lumen, wherein the second tubular stent body is disposable within a second ureter;
   (d) a second retention structure extending from a distal end of the second tubular stent body, wherein the second retention structure is disposable within a second kidney; and
   (e) an elongate connection member comprising:
      (i) a first length comprising:
         (A) a first end extending from a proximal end of the first tubular stent body, wherein the first end and the first tubular stent body form a first single unitary component; and
         (B) a first magnet coupled to the first length; and
      (ii) a second length comprising:
         (A) a second end extending from a proximal end of the second tubular stent body, wherein the second end and the second tubular stent body form a second single unitary component; and
         (B) a second magnet coupled to the second length, wherein the second magnet is magnetically coupleable with the first magnet such that the first and second lengths are coupled together within a bladder of a patient.

6. The ureteral stent of claim 5, wherein the connection member is configured to prevent distal migration of the first and second tubular stent bodies.

7. A method of promoting flow of urine to a bladder of a patient, the method comprising:
inserting a first guidewire into a first kidney via a first ureter;
inserting a second guidewire into a second kidney via a second ureter;
urging a first tubular stent body distally on the first guidewire until a first retention structure extending from a distal end of the first tubular stent body is disposed in the first kidney, wherein the first tubular stent body comprises:
(a) a first lumen; and
(b) a first connection member extending from a proximal end of the first tubular stent body such that the first tubular stent body and the first connection member form a first single unitary component, the first connection member comprising a first coupling structure;
urging a second tubular stent body distally on the second guidewire until a second retention structure extending from a distal end of the second tubular stent body is disposed in the second kidney, wherein the second tubular stent body comprises:
(a) a second lumen; and
(b) a second connection member extending from a proximal end of the second tubular stent body such that the second tubular stent body and the second connection member form a second single unitary component, the second connection member comprising a second coupling structure; and
coupling the first coupling structure to the second coupling structure such that the first and second connection members are disposed entirely within the bladder when the first retention structure is disposed in the first kidney and the second retention structure is disposed in the second kidney.

8. The method of claim 7, further comprising magnetically coupling the first coupling structure to the second coupling structure in the bladder.

9. The method of claim 7, further comprising urging the first and second connection members proximally out of the bladder to remove the first and second connection members, the first tubular stent body, and the second tubular stent body from the patient.

10. The method of claim 7, wherein the first and second connection members prevent distal migration of the first and second tubular stent bodies.

11. The ureteral stent of claim 1, wherein the first tubular stent body, the second tubular stent body, and the elongate connection member are sized such that the elongate connection member and the proximal ends of the first and second tubular stent bodies are disposed entirely within the bladder.

12. The ureteral stent of claim 1, wherein the first and second lengths are magnetically coupleable.

13. The ureteral stent of claim 5, wherein the first tubular stent body, the second tubular stent body, and the elongate connection member are sized such that the elongate connection member and the proximal ends of the first and second tubular stent bodies are disposed entirely within the bladder.

14. The ureteral stent of claim 5, further comprising openings defined in the first tubular stent body and the second tubular stent body.

15. The ureteral stent of claim 14, wherein the openings provide fluidic access to the first and second lumens.

16. The method of claim 7, wherein the first tubular stent body, the second tubular stent body, and the first and second connection members are sized such that the first and second connection members and the proximal ends of the first and second tubular stent bodies are disposed entirely within the bladder.

17. The method of claim 7, further comprising openings defined in the first tubular stent body and the second tubular stent body.

18. The ureteral stent of claim 17, wherein the openings provide fluidic access to the first and second lumens.

* * * * *